United States Patent [19]

Matsuura et al.

[11] Patent Number: 4,497,323

[45] Date of Patent: Feb. 5, 1985

[54] EXHAUST VALVE HAVING A CONSTANT BLEED RATE

[75] Inventors: Masahiro Matsuura; Tsutomu Ichinomiya; Hideaki Abe, all of Shiga, Japan

[73] Assignee: Matsushita Electric Works, Ltd., Kadoma, Japan

[21] Appl. No.: 425,914

[22] Filed: Sep. 28, 1982

[30] Foreign Application Priority Data

Nov. 14, 1981 [JP] Japan .................. 56-182876

[51] Int. Cl.³ ............................... A61B 5/02
[52] U.S. Cl. ..................... 128/685; 251/149.1
[58] Field of Search .......... 128/672, 677, 685; 251/149, 149.1, 149.8, 153; 137/498, 843, 845

[56] References Cited

U.S. PATENT DOCUMENTS

| 3,567,175 | 3/1971 | Sciuto, Jr. | 251/149.6 |
| 3,779,236 | 12/1973 | Stewart | 128/685 |
| 3,893,478 | 7/1975 | Peters | 128/685 X |
| 3,918,437 | 11/1975 | Saba | 128/685 |
| 4,037,587 | 7/1977 | Kaneda et al. | 128/685 |
| 4,198,031 | 4/1980 | Ezekiel et al. | 128/685 X |
| 4,200,259 | 4/1980 | Ueda | 128/685 X |
| 4,326,536 | 4/1982 | Kitagawa et al. | 128/682 |
| 4,402,340 | 9/1983 | Lockwood, Jr. | 251/149.8 X |

FOREIGN PATENT DOCUMENTS 2076941 12/1981 United Kingdom .......... 128/685

Primary Examiner—Lee S. Cohen
Assistant Examiner—Angela D. Sykes
Attorney, Agent, or Firm—Stevens, Davis, Miller & Mosher

[57] ABSTRACT

Disclosed is an exhaust valve having an approximately constant rate of pressure loss per unit time which is particularly useful with an automatic sphygmomanometer. A pair of abutting plates are provided in a fluid flow path. The plates are pressurized into contact with each other at least in part by a pressurized fluid to be exhausted through the valve. At least one of the plates is formed of a resilient material and a gap-forming member is disposed between the abutting plates to define an exhaust passage which has a cross section which varies as the pressure of the pressurized fluid varies.

12 Claims, 16 Drawing Figures

EXHAUST VALVE HAVING A CONSTANT BLEED RATE

BACKGROUND OF THE INVENTION

This invention relates to an exhaust valve and, in particular, to a slow release valve for use with an automatic sphygmomanometer which measures human blood pressure.

An automatic sphygmomanometer which uses an exhaust valve is shown in FIG. 1. A cuff and a pressurizing pump for feeding air into the cuff, indicated by reference numerals 21 and 22, respectively, are provided, between which an exhaust valve 1 for slow exhaust and another exhaust valve 23 for rapid exhaust are interposed. Valves 1 and 23 are fluidically connected with each other as well as with the cuff and the pump, the cuff 21 being also connected to a pressure detecting means 24 composed of a bellows and a differential transformer. Reference numeral 25 indicates a microphone for sound detection, 26 an amplifier, 27 a low-pass filter, 28 a band-pass filter, 29 a level detecting circuit, 30 a Korotkoff's sound discriminator, 31 an operation control circuit, 32 a converter, 33 a pulse frequency computation circuit, 34 a memory circuit for storing maximum and minimum blood pressure and pulse frequency values, and 35 a display for displaying these values.

During operation of the FIG. 1 apparatus, air pressure in the cuff is increased to exceed the maximum blood pressure value, and then is gradually reduced by bleeding air through the slow release exhaust valve 1. After maximum and minimum blood pressure measurements and a pulse frequency measurement are taken, the air in the cuff 21 is rapidly exhausted through the rapid exhaust valve 23.

It is generally known that when measuring blood pressure, discrimination of Korotkoff's sounds using an automatic sphygmomanometer according to the Riva-Rocci-Korotkoff method is most easily done when the slow release exhaust rate, e.g. the release rate through exhaust valve 1 in FIG. 1, is about 2 to 3 mmHg/sec. However, it is impossible to maintain an optimum exhaust rate under a wide range of pressure conditions because conventional slow release exhaust valves in general have a device such as a plate in which a small exhaust hole is bored which causes a rapid exhaust when the air pressure is high, but a slower exhaust when the air pressure is low, as shown in FIG. 5.

SUMMARY OF THE INVENTION

An object of the invention is the provision of an exhaust valve having a configuration which enables it to bleed air at an approximately constant rate of pressure loss per unit time regardless of the air pressure.

An additional object of the invention is the provision of an exhaust valve which is highly resistant to damage due to external shocks caused, for example, by dropping or vibration of the valve.

These objects and advantages of the invention and others will be clearly seen from the following description of the invention which is provided in connection with the accompanying drawings.

DETAILED DESCRIPTION OF THE INVENTION

Figure 1:
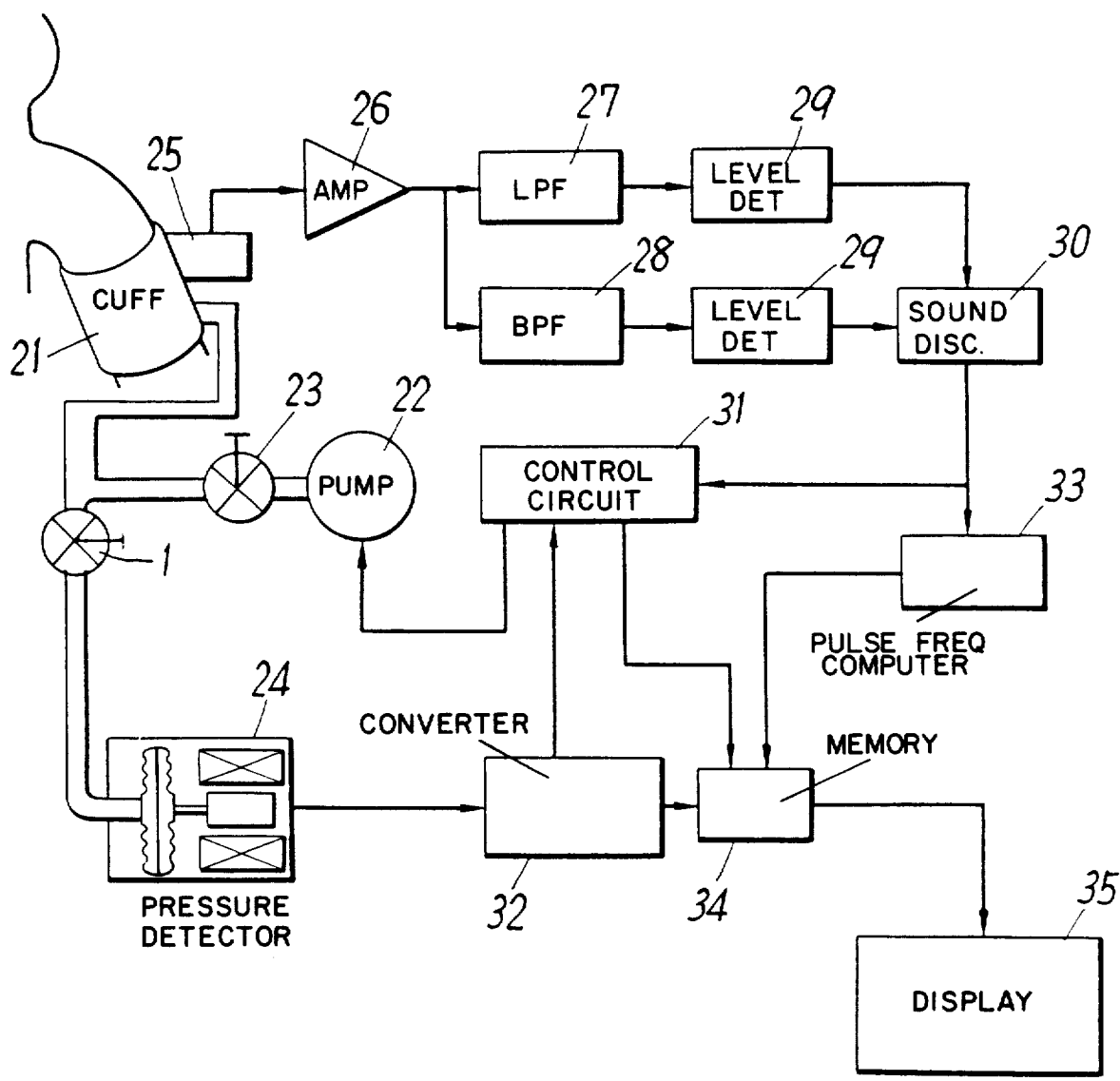
FIG. 1 is a block diagram of an automatic sphygmomanometer which may employ an exhaust valve of the invention.
Figure 2:
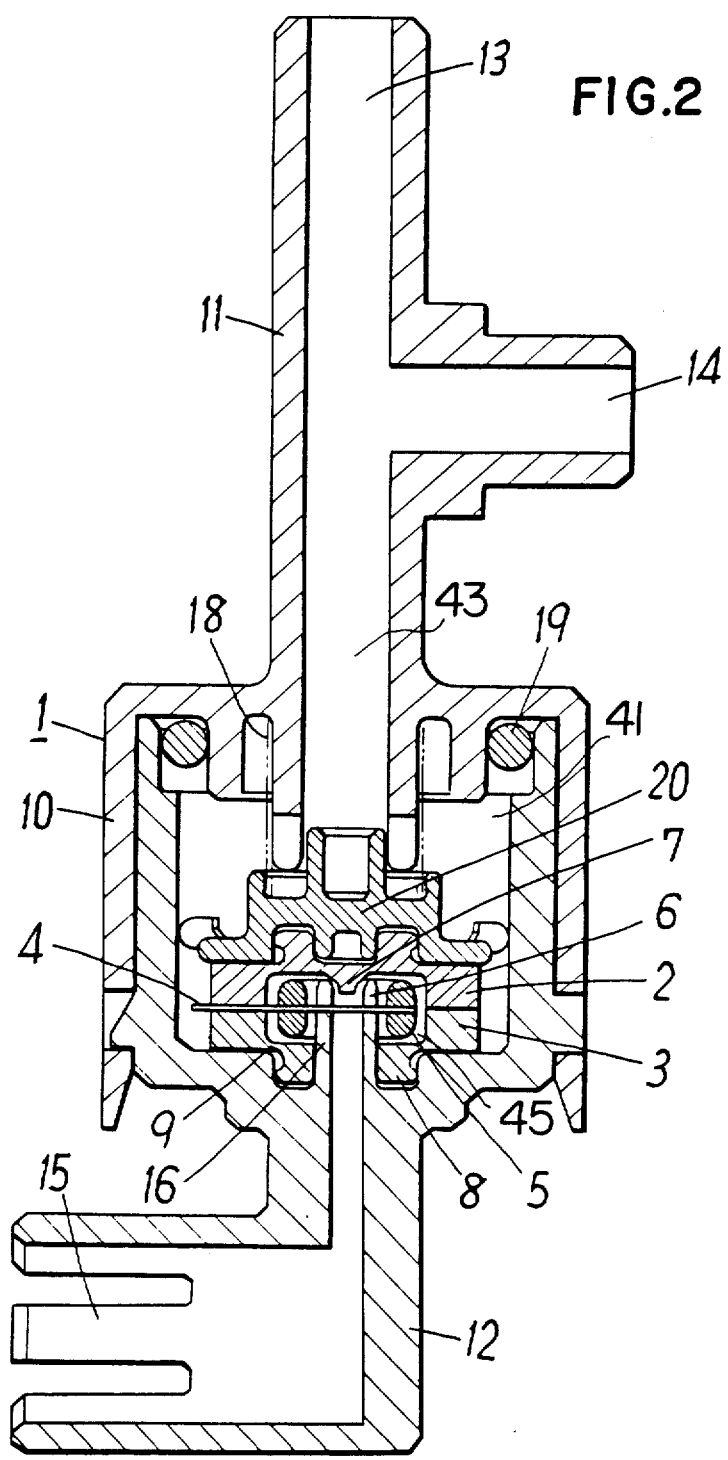
FIG. 2 is a cross sectional view of a first embodiment of the invention.
Figure 3:
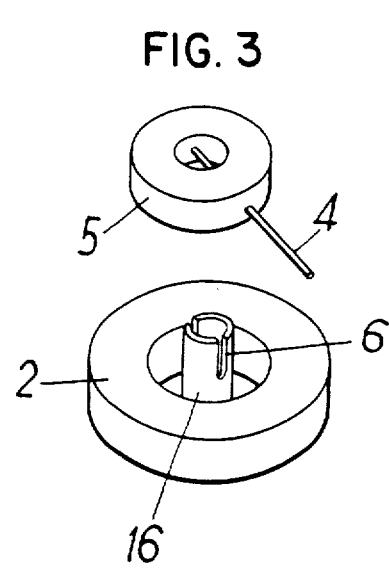
FIG. 3 is a perspective view of a portion of the first embodiment illustrated in FIG. 2.

FIGS. 2 and 3 show a first embodiment of an exhaust valve constructed in accordance with the teachings of this invention. Reference numeral 10 indicates a casing composed of a pair of cylindrical bodies 11 and 12, cylindrical body 11 being provided with an opening 13 for fluid connection with the cuff 21 (FIG. 1), and another opening 14 for fluid connection with the exhaust valve 23 and the pressurizing pump 22 (FIG. 1). The cylindrical body 12 is provided with an exhaust port 15. One end of the cylindrical body 12 is inserted into the cylindrical body 11 and is provided with a recess 41 having an open end which is sealed with an O-ring 19. O-ring 19 engages with and seals a space between cylindrical bodies 11 and 12. An exhaust pipe 16, which communicates with the exhaust port 15, is provided within cylindrical body 12 and projects into recess 41. A valve unit is formed by a pair of resilient plates 2 and 3 and a gap-forming member 4 is interposed between plates 2 and 3. One resilient plate 3 of the two is provided with a sealing part 8 formed integrally with the plate with a thin-walled part 9 connecting them. Resilient plate 3 is secured to the exterior of the exhaust pipe 16 so that the sealing part 8 is in tight contact therewith. The other plate 2 is placed over plate 3 and is biassed toward plate 3 by means of a spring 18 and air pressure within a passage way 43 of cylindrical body 11 which act on a support 20. Support 20 pushes plate 2 into tight contact with the plate 3. The gap-forming member 4 is interposed between the resilient plates 2 and 3 and forms a gap which serves as an exhaust route therebetween from the recess 41 through an exhaust passage 45 to the exhaust pipe 16. It is composed of a needle-like pin of about 0.15 mm diameter which is provided with an annular stopper 5 into which the exhaust pipe 16 is inserted. The gap-forming member 4 is positioned within a slit 6 (FIG. 3) provided on the upper end of the exhaust pipe 16.

Figure 4A:
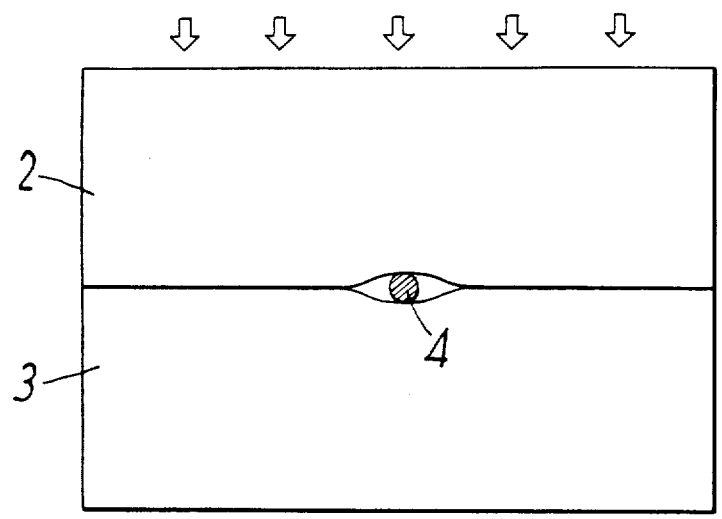
FIGS. 4(a) and 4(b) are views of another portion of the first embodiment of the invention illustrating its operation.
Figure 4B:
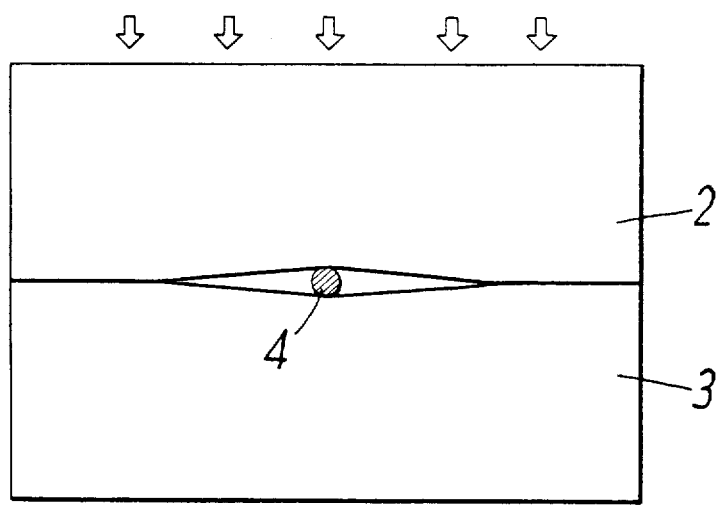
Figure 5:
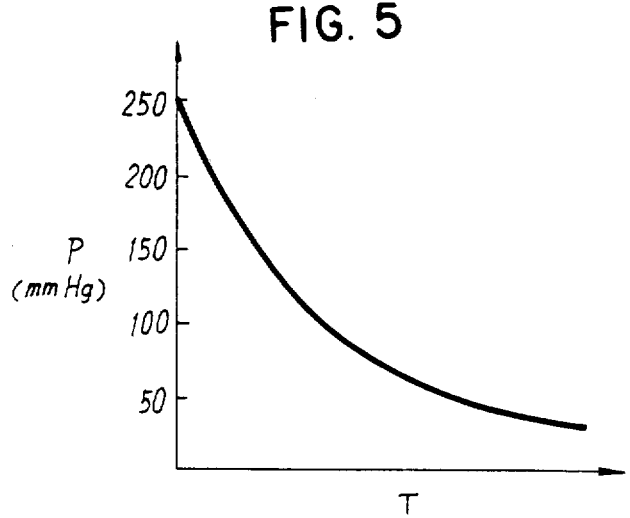
FIG. 5 is a diagram showing the exhaust characteristic of the valve unit of a conventional exhaust valve.
Figure 6:
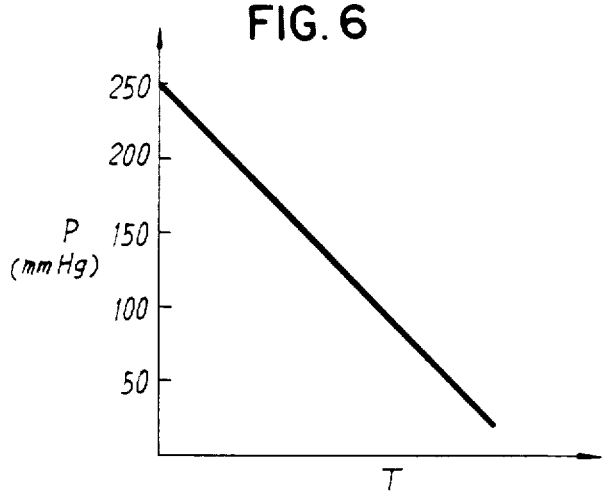
FIG. 6 is a diagram showing the exhaust characteristic of a valve unit of an exhaust valve constructed in accordance with the teachings of the invention.

When the air pressure applied to the upper surface of the valve support 20 is high, the pressure applied to plates 2 and 3 by support 20 is likewise high and the volume deformation of the resilient plates 2 and 3 is large causing the cross sectional area of the gap produced by the presence of the gap-forming member 4 to be small, as shown in FIG. 4. With a decrease in pressure, the volume deformation of the resilient plates is reduced and the cross sectional area of the gap increases. As a result, an approximately constant rate of pressure loss, as shown in FIG. 6, is maintained through plates 2 and 3 regardless of variations in the air pressure which is being exhausted.

If the gap-forming member 4 has a large degree of movement freedom, any impact on the FIG. 2 valve construction could cause the gap-forming member 4 to be ejected from between the resilient plates 2 and 3. It may be displaced in one direction until a first end thereof is stopped by the inner wall of the casing 10, or it may be displaced in an opposite direction until the other end thereof is caught between the plates 2 and 3.

Figure 8A:
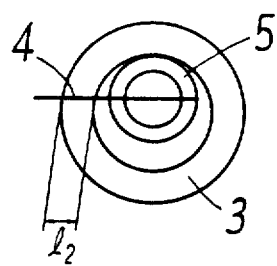
FIGS. 8(a) and 8(b) are partial plan views of a portion of the second embodiment of the invention illustrating its operation.
Figure 8B:
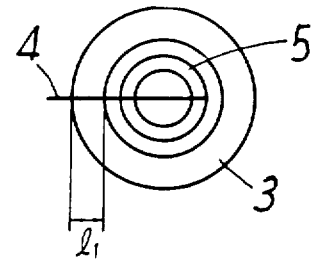

To prevent this from occurring, stopper 5 is provided in the exhaust passage 45 between the resilient plates 2 and 3, so that the contact of the inner surface of the annular stopper 5 with the exhaust pipe 16 and the contact of the outer surface of the stopper 5 with the inner surfaces of the resilient plates 2 and 3 controls the lengthwise movement of the gap-forming member 4, restricting it according to the radii of the exterior of the exhaust pipe 16 and the interior of the exhaust passage 45 between resilient plates 2 and 3. Slit 6 is also provided at the end of exhaust pipe 16 through which the gap-forming member passes. The positioning of the gap-forming member 4 in the slit 6 also prevents the displacement of the gap-forming member 4 in the horizontal direction perpendicular to the length thereof beyond the point where the fixed transverse length $l_1$ along the contacting surface between the resilient plates 2 and 3 as shown in FIG. 8(b) is changed to a transverse length $l_2$ as shown in FIG. 8(a).

Figure 7:
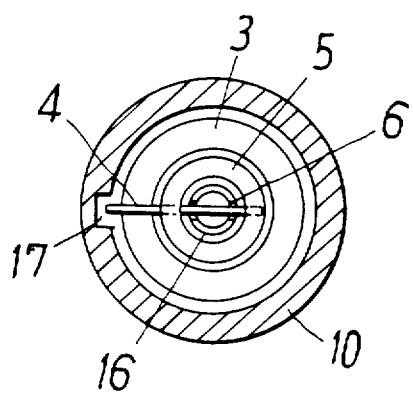
FIG. 7 is a horizontal cross sectional view of a second embodiment of the invention.

FIG. 7 illustrates a modified construction having a recess 17 on the inner surface of the casing 10 for receiving the tip of the gap-forming member 4.

As noted above, the resilient plate 3 is provided with a sealing part 8 which contacts with the outer periphery of exhaust pipe 16 to prevent air leakage from recess 41 to the exhaust passage 45, however, when strain caused during the fitting of the sealing part 8 on exhaust pipe 16 develops it will cause irregularities in the contacting of the surface of the plate 3 with that of the plate 2, causing fluctuations in the exhaust rate to occur. The thin-walled part 9 between the main part and the sealing part 8 of plate 3 absorbs the strain described above and helps maintain a uniform contact between resilient plates 2 and 3.

A projection 7 is preferably provided on the resilient plate 2, extends toward the exhaust passage between the resilient plates 2 and 3, and is positioned in the end of the opening of the exhaust pipe 16 to prevent the gap-forming member 4 from jumping out of the slit 6 should the exhaust valve receive an external impact.

Figure 9A:
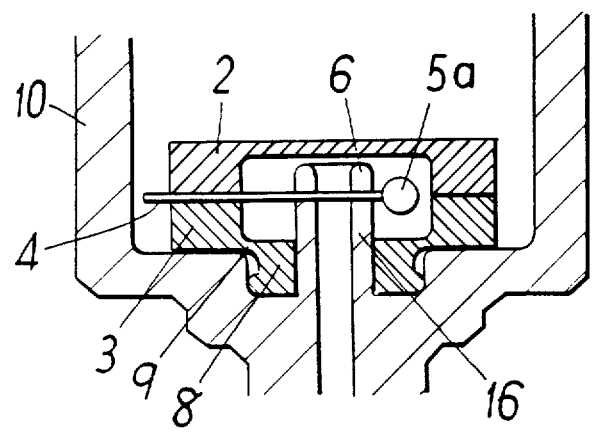
FIGS. 9(a) and 9(b) are a cross sectional view and a perspective view, respectively, of a third embodiment of the invention.
Figure 9B:
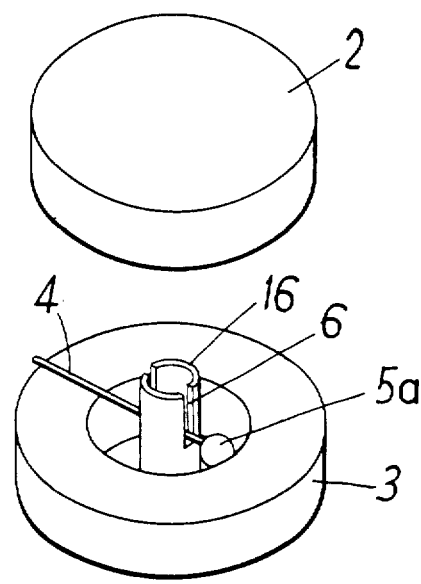
Figure 10:
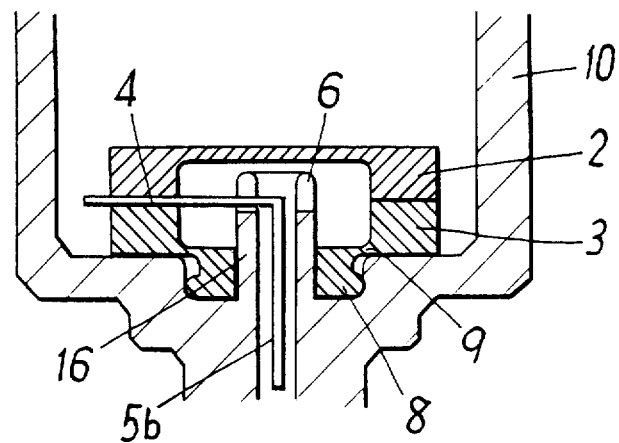
FIG. 10 is a cross sectional view of a fourth embodiment of the invention.

FIGS. 9(a) and 9(b) show another embodiment of this invention, in which one end of the linear gap-forming member 4 is provided with a spherical stopper 5a which prevents gap-forming member 4 from being displaced longitudinally beyond a range permitted by the displacement of the stopper 5a between the exterior of the exhaust pipe 16 and the interior of the resilient plates 2 and 3. This purpose may also be fulfilled by bending one end of the linear gap-forming member 4 at a right angle so that it can be inserted into the exhaust pipe 16 through the slit 6 as shown in FIG. 10. In this case, the bent end of the gap-forming member 4 serves as a stopper 5b constrained to move within the interior of the exhaust pipe 16.

Figure 11A:
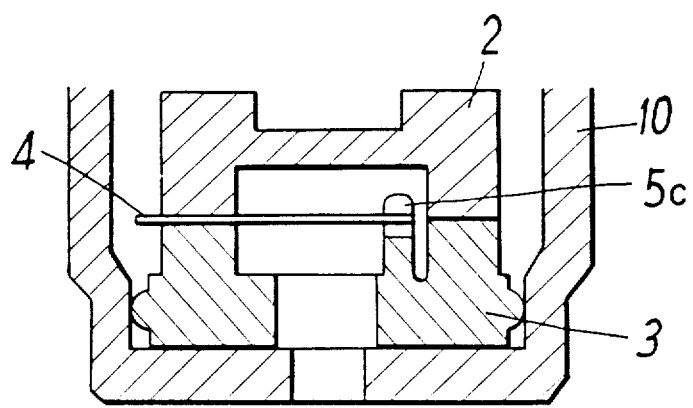
FIGS. 11(a) and 11(b) are a cross sectional view and a perspective view, respectively, of a fifth embodiment of the invention.
Figure 11B:
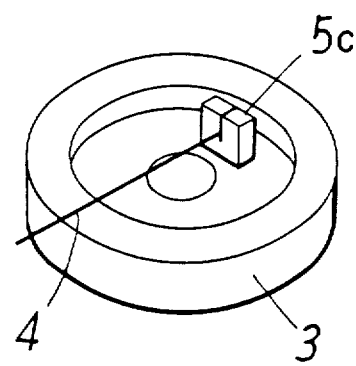

As another variant shown in FIG. 11, a clamping part ay be used as a stopper 5c, the clamping part being formed integrally with the resilient plate 3 for the insertion and positive retention of one end of the gap-forming member.

Figure 12:
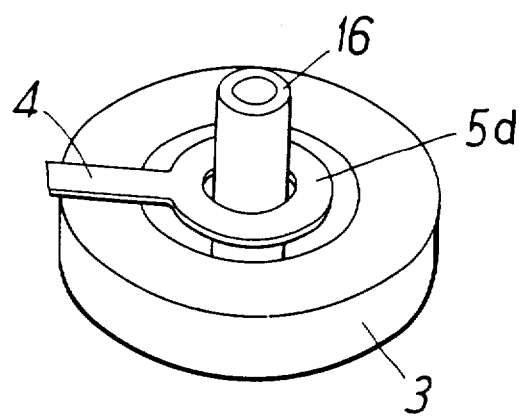
FIG. 12 is a perspective view of a sixth embodiment of the invention.

FIG. 12 shows another embodiment employing an annular stopper 5d which surrounds exhaust pipe 16. Stopper 5d is made of a thin plate integrally with the gap-forming member 4 and has the advantages of allowing for less play while using a simple structure. Displacement of gap-forming member 4 is limited by the space between the exterior of exhaust pipe 16 and the interior of stopper 5d.

In the above described embodiments, the pair of resilient plates 2 and 3 are made of a resilient material such as silicone rubber or NBR, however, the objects and advantages of this invention can be achieved even when one of the two plates is made of rigid material and the other of a resilient material.

As has been described heretofore, this invention provides a structure in which a gap-forming member 4 interposed between a pair of abutting plates which are brought into close contact with each other at least in part by air fed into the valve, provides an exhaust route between the plates. The gap thus formed varies in cross sectional area in response to fluctuations in air pressure so as to keep the rate of pressure loss approximately constant. A stopper, provided in the exhaust passage, prevents the gap-forming member from being displaced beyond a fixed range, thereby ensuring a constant rate of pressure loss while restricting the movement of the gap-forming member which might cause fluctuations in the cross sectional area of the gap.

Although various embodiments of the invention have been shown and described, the invention is not limited by the foregoing description as many modifications may be made without departing from the spirit and scope of the invention.

What is claimed is:

1. An exhaust valve comprising a first passage for receiving a fluid to be exhausted, a second passage for exhausting said fluid, a pair of abutting plates interposed in a fluid flow path between said first and second passages, means for biassing said pair of plates into pressurized contact with each other at least in part by a pressurized fluid in said first passage, at least one of said plates being formed of a resilient material, and a gap-forming member interposed between said abutting plates and forming a gap between said plates which serves as a variable flow exhaust path between said first and second passages.

2. An exhaust valve as set forth in claim 1, wherein both of said abutting plates are formed of resilient materials.

3. An exhaust valve as set forth in claim 1, wherein said gap-forming member is provided with a stopper and further comprising means cooperating with said stopper to limit displacement of said gap-forming member.

4. An exhaust valve as set forth in claim 3, further comprising an exhaust pipe projecting into said second passage, said stopper being shaped into a ring to which said gap-forming member is fixed, said ring surrounding said exhaust pipe.

5. An exhaust valve as set forth in claim 3 further comprising an exhaust pipe projecting into said second passage, said stopper being formed as a ring-like thin plate surrounding said exhaust pipe which is formed integrally with said gap-forming member.

6. An exhaust valve as set forth in claim 3 further comprising an exhaust pipe disposed in said second passage, said stopper being formed as a bent end of said gap-forming member which is inserted into said exhaust pipe.

7. An exhaust valve as set forth in claim 3 wherein said stopper is formed as a spherical element provided on one end of said gap-forming member.

8. An exhaust valve as set forth in claim 1, wherein said gap-forming member is needle-shaped.

9. An exhaust valve as set forth in claim 1 further comprising a casing defining the exterior of said exhaust valve, and an exhaust pipe having an end projecting into said second passage, said gap-forming member having a first end which is inserted into a recess formed on an inner wall of said casing and a second end which is retained in a recess provided within said projecting end of said exhaust pipe.

10. An exhaust valve as set forth in claim 9, wherein a projection is provided on one of said pair of abutting plates and is disposed in an opening within said projecting end of the exhaust pipe to retain said gap-forming member in the recess provided within said projecting end of the exhaust pipe.

11. An exhaust valve as set forth in claim 1 further comprising an exhaust pipe having an end projecting through one of said plates and into said second passage, a sealing part comprising a resilient material fitted on an outer periphery of said projecting end of the exhaust pipe in said second passage, said sealing part and said at least one abutting plate formed of a resilient material being formed integrally and continuously with each other through a thin-walled part.

12. An exhaust valve as set forth in claim 1 further comprising resilient biassing means for biassing said abutting plates together.

* * * * *